United States Patent [19]

Van Overloop

[11] Patent Number: 5,005,754
[45] Date of Patent: Apr. 9, 1991

[54] BLADDER AND MANDREL FOR USE WITH SURGICAL STAPLER

[75] Inventor: Ronald R. Van Overloop, West Chester, Ohio

[73] Assignee: Ethicon, Inc., Somerville, N.J.

[21] Appl. No.: 504,774

[22] Filed: Apr. 4, 1990

[51] Int. Cl.⁵ ............................................. A61B 17/00
[52] U.S. Cl. .................................................. 227/178
[58] Field of Search ................................. 227/175, 178

[56] References Cited

U.S. PATENT DOCUMENTS 4,869,414  9/1989  Green et al. .................... 227/120 X

FOREIGN PATENT DOCUMENTS 101310  2/1984  European Pat. Off. ............ 227/178
324635  7/1989  European Pat. Off. ............ 227/175
324636  7/1989  European Pat. Off. ............ 227/175
324638  7/1989  European Pat. Off. ............ 227/175

Primary Examiner—Timothy V. Eley
Attorney, Agent, or Firm—Paul A. Coletti

[57] ABSTRACT

A disposable mandrel and bladder is shown in which the mandrel is injected molded or machine fabricated in some other way that allows it to be permanently incorporated within the driver bladder of a surgical stapling mechanism. Supply line tubing is an integral part of the mandrel and would thus be permanently bonded to the bladder sub-assembly. Such configuration prevents tube clogging, bladder folding over infusion lines, and produces reliable firing of the stapler while using pneumatic driving mechanism.

6 Claims, 5 Drawing Sheets

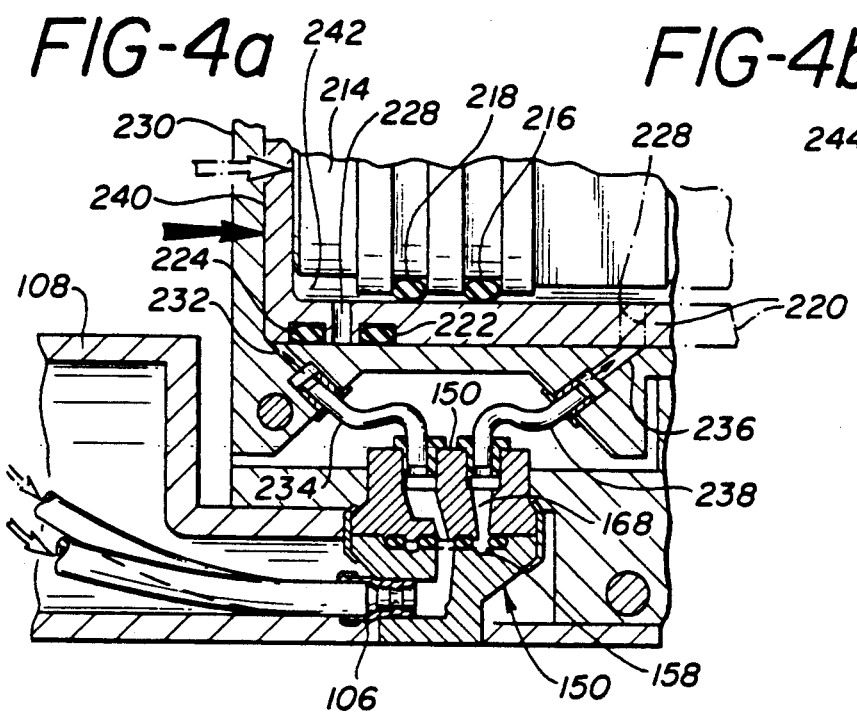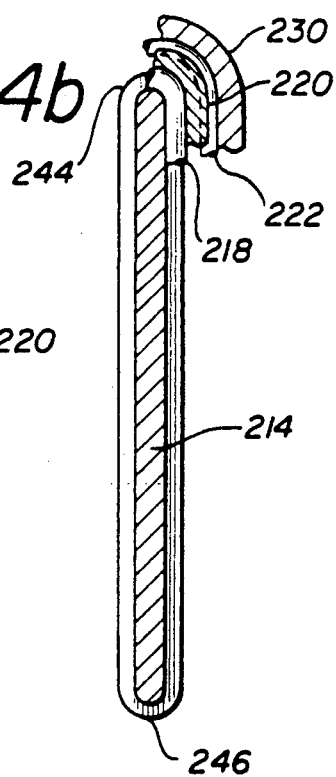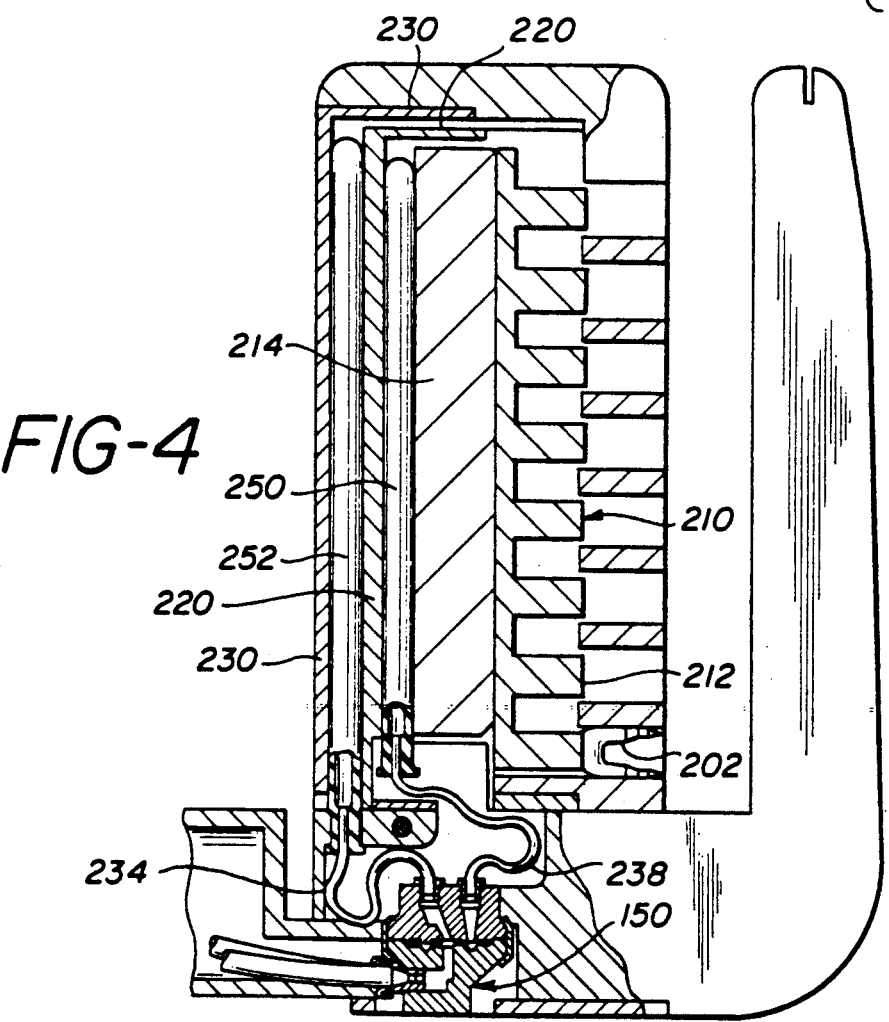

BLADDER AND MANDREL FOR USE WITH SURGICAL STAPLER

FIELD OF THE INVENTION

This invention relates to surgical stapling instruments. More specifically, this invention relates to pneumatically powered surgical staplers. Most specifically, this invention relates to the driving mechanism used in connection with pneumatically powered surgical staplers.

BACKGROUND OF THE INVENTION

Pneumatic surgical staplers have become one of the preferred alternative methods to manually driven surgical staplers. An advantage of a pneumatic surgical stapler is that the force needed to fire the stapler is controlled by the driving mechanism, and not the strength of the user. In a pneumatic stapler, a compressed gas line or compressed gas cartridge releases gas pressure in order to activate the driving mechanism in the surgical stapler. In a reliable pneumatically driven surgical stapling mechanism, the force required to fire the staple is repeatably derived within a very refined tolerance. Thus, in a pneumatic surgical stapler there is the assurance that a repeatable force-to-fire is derived.

One of the ways in which pneumatic surgical staplers operate is through means of an inflatable elastomeric bladder. Bladders convert pneumatic pressure into motion within the limitably accessible head of the surgical stapler. A bladder operates by expanding from pressurized fluid inserted into an opening in the bladder. The fluid is generally carbon dioxide gas and is introduced through a tube inserted in the opening in one end of a sock-like bladder. The tube and bladder have previously been connected to each other by means of a mechanical clamp. The bladder forms a type of gasket between the clamping parts and the tube.

Introduction of carbon dioxide causes inflation of the bladder and can be converted to movement of various mechanisms in, for example, the head of a linear surgical stapler.

For the stapler to be a limited access device, the combination of bladder, tubing and stapling head must meet severe dimensional constraints. The bladder, tubing and driving mechanism must all fit within a linear stapling head which fits within the body. In general, the typical bladders used have a bottle-necked configuration which permits the smallest union between tube, bladder and clamping mechanism.

Bladders are made in a variety of ways including a latex dipping process using a mandrel. The mandrel has the configuration of the interior of the bladder and is dipped into liquid latex. The later is allowed to cure or solidify around the mandrel, resulting in a bladder.

A manufacturing problem is encountered in the necked region of the bladder. At this neckdown, it is extremely difficult to remove the bladder from the mandrel. The generally elastomeric latex bladder must be stretched over the shoulders of a mandrel and pulled from the bottom of the necking configuration. This procedure is time consuming and labor intensive and adds to the cost of making the part.

In addition, this assembly must be made in a tight fit, particularly since addition of any lubricant for tube insertion within the bladder combination may jeopardize later function of the stapling assembly.

Also, after firing, rapid deflation of the bladder in the stapling head can result in bladder material closing the orifice of a supply tube. Fluid becomes trapped when this orifice is blocked before complete deflation/inflation. Total deflation is limited due to the sealing off of the bladder material.

Additionally, dimensional interference between the clamping mechanism which holds the bladder on the tube and the tubing mechanism which inflates the bladder can result in crimping of the tubing mechanism. This results in flow restriction and decreased speed of closure of the clamping mechanism.

It is necessary to correct these problems for pneumatic stapling to be a desirable alternative procedure.

SUMMARY OF THE INVENTION

It is therefore an object of the invention to provide a bladder and mandrel combination useful in a pneumatic surgical stapler.

It is further an object of the invention to provide a bladder and mandrel combination useful within a typical linear surgical stapler head.

It is yet another object of the invention, to provide a bladder and mandrel combination useful in a pneumatic surgical stapler wherein the mandrel and bladder are configured so as to prevent clogging, improper clamping, non-vacating of the mechanism, collapsing of the bladder, and other functional problems.

These and other objects of the invention are accomplished in a bladder and mandrel combination wherein the mandrel and bladder are permanently incorporated with one another. Supply line tubing of the mandrel forms an integral part of the mandrel and it becomes permanently bonded to a bladder sub-assembly. Elastomeric bladder material is coated on the mandrel by means of any suitable fabrication technique. The bladder material is bonded to the mandrel neck while permitting inflation separation in the functional areas of the bladder. The loosened fit on the stapler clamping mechanism on the bladder also results in improved flow.

These and other objects of the invention are realized in the accompanying Detailed Description of the Drawings taken in connection with the Detailed Description of the Invention which follows.

DETAILED DESCRIPTION OF THE DRAWINGS

FIG. 4 is a cross-sectional view of a bladder combination;

FIG. 4a is a cross-sectional view of the connection of the stapling head as seen in FIG. 3;

FIG. 4b is a cross-sectional view of the head in FIG. 3;

DETAILED DESCRIPTION OF THE INVENTION

Figure 1:
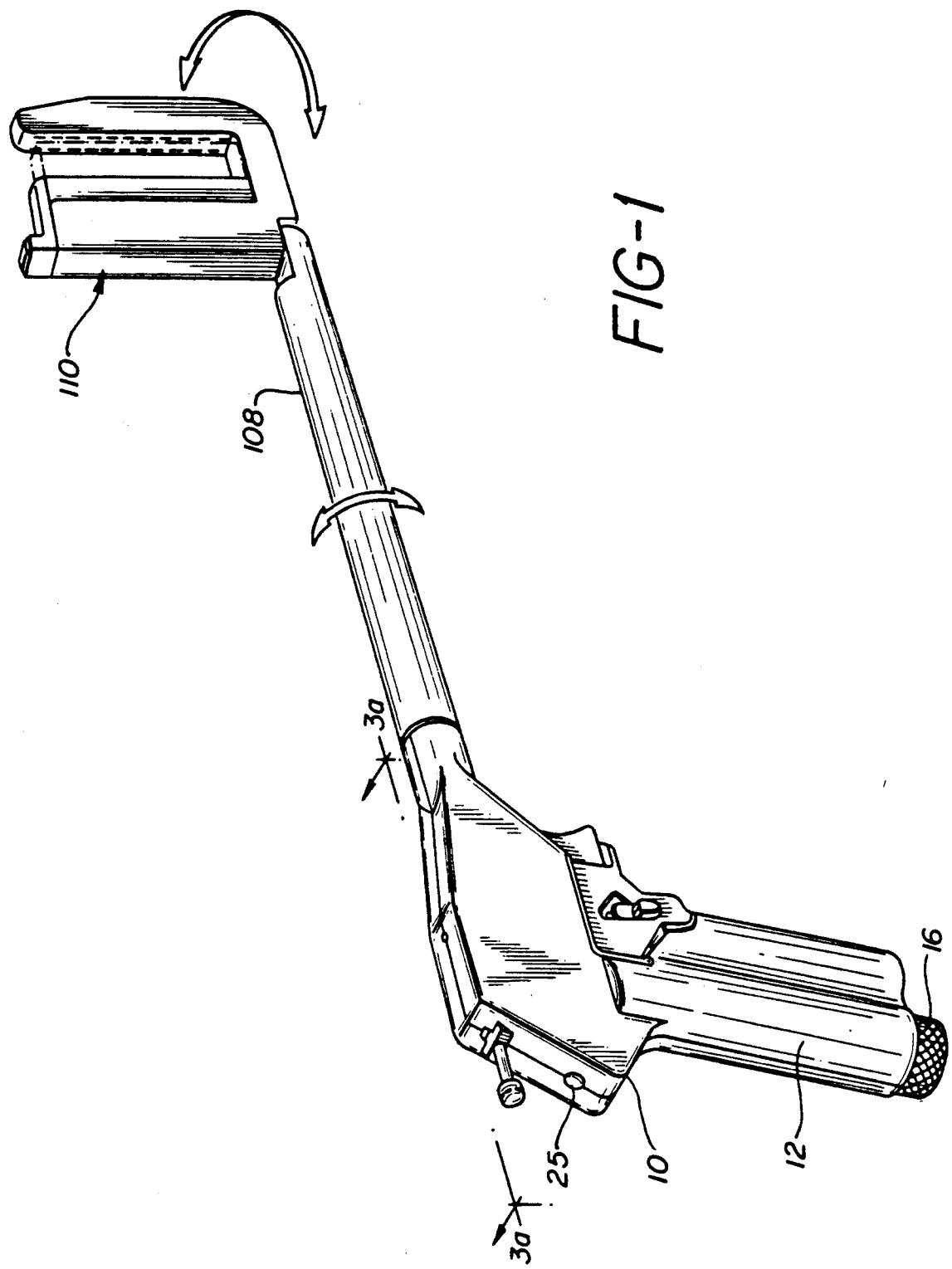
FIG. 1 is a perspective view of a typical pneumatic linear surgical stapler.

Referring first to FIG. 1, a gas-powered surgical stapler of the invention is shown. The stapler includes three major components: a handle portion 10, a neck portion 108, and a stapler head 110. The three components are joined at their interconnecting points by pneumatic quick-disconnect fittings which allow the components to be disconnected and interchanged. Also located at the joints are pneumatic rotating unions, which allow free rotation of the components with respect to each other, as indicated by the arrows in FIG. 1.

Figure 2:
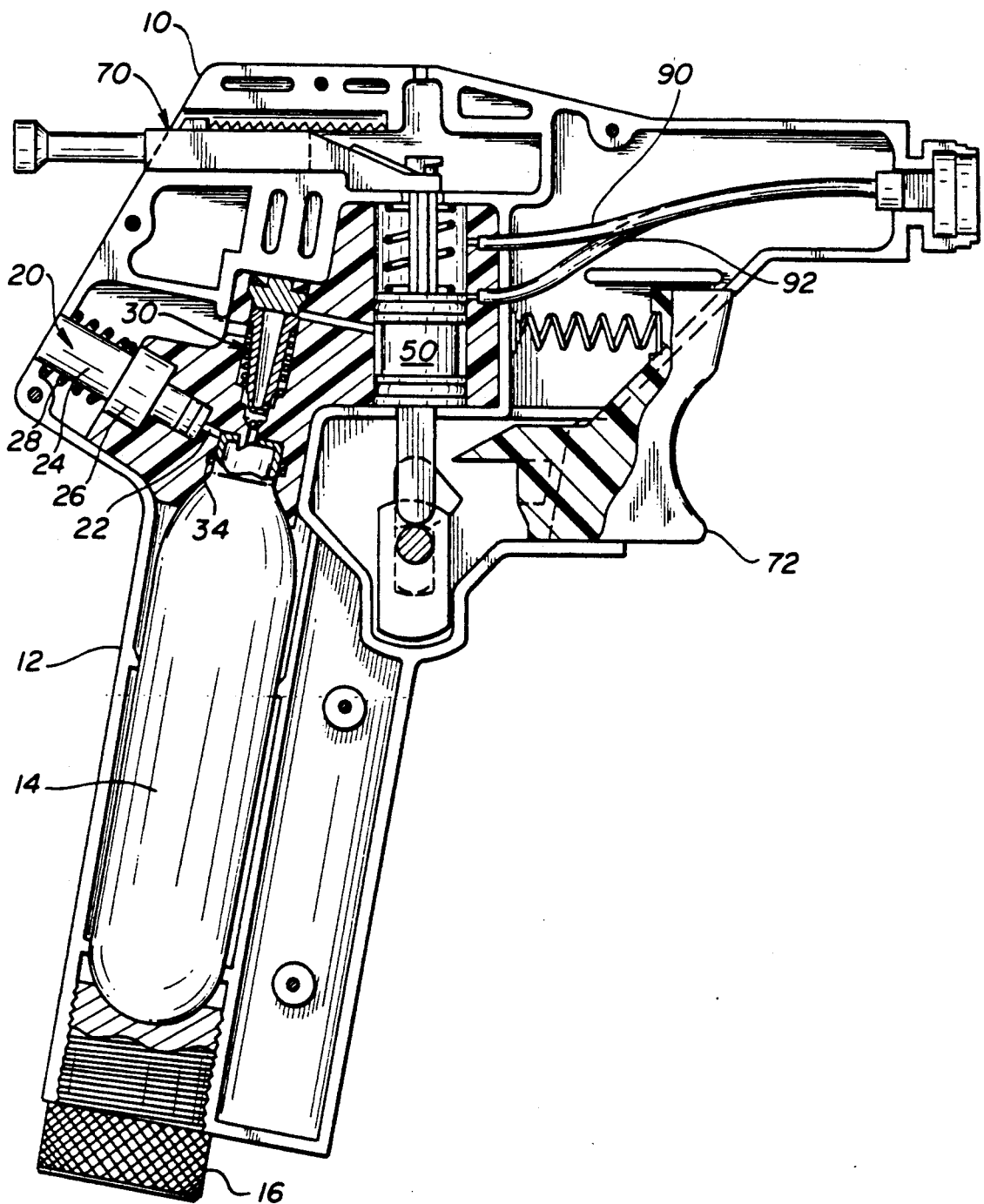
FIG. 2 is a cross-section of the firing mechanism along lines 2—2 of FIG. 1.

As in FIGS. 1 and 2, the handle portion 10 is a subassembly which contains a pressurization indicator 20, a pressure regulator 30, a pressure distribution spool 50 and a firing sequence mechanism 70. The lower pistol grip section 12 of the handle 10 contains a compartment for a pressurized carbon dioxide gas cylinder 14. The cylinder 14 is inserted into the pistol grip section from the bottom, and a threaded cap 16 is tightened to secure the cylinder in its compartment. As the cap is tightened the top of the cylinder is pierced and pressurized gas is released into the stapler. Pressurized gas is released at the cylinder pressure (approximately 800 psi) and initially the gas pressurizes a chamber 34 within the stapling handle 10. This gas pressure passes through a passageway 22 to pressurization indicator 20.

The pressurization indicator 20 includes a cylinder 24 located in a chamber at the rear of the handle which is sealed in the chamber by an O-ring 26 prior to pressurization. The end 25 of the cylinder is flush with the outer surface of the handle and is retained in this position by the force of the spring 28.

The pressure distribution spool 50 provides a means for applying pressurized gas to operative parts of the stapler during a stapling procedure. Pressurized gas is needed during two phases of operation. One is the clamping cycle, when tissue being stapled is clamped between the jaws or other closing parts of the stapler head. The other is the staple cycle, when staples are driven through the tissue and formed in fixed positions in the tissue.

Figure 3:
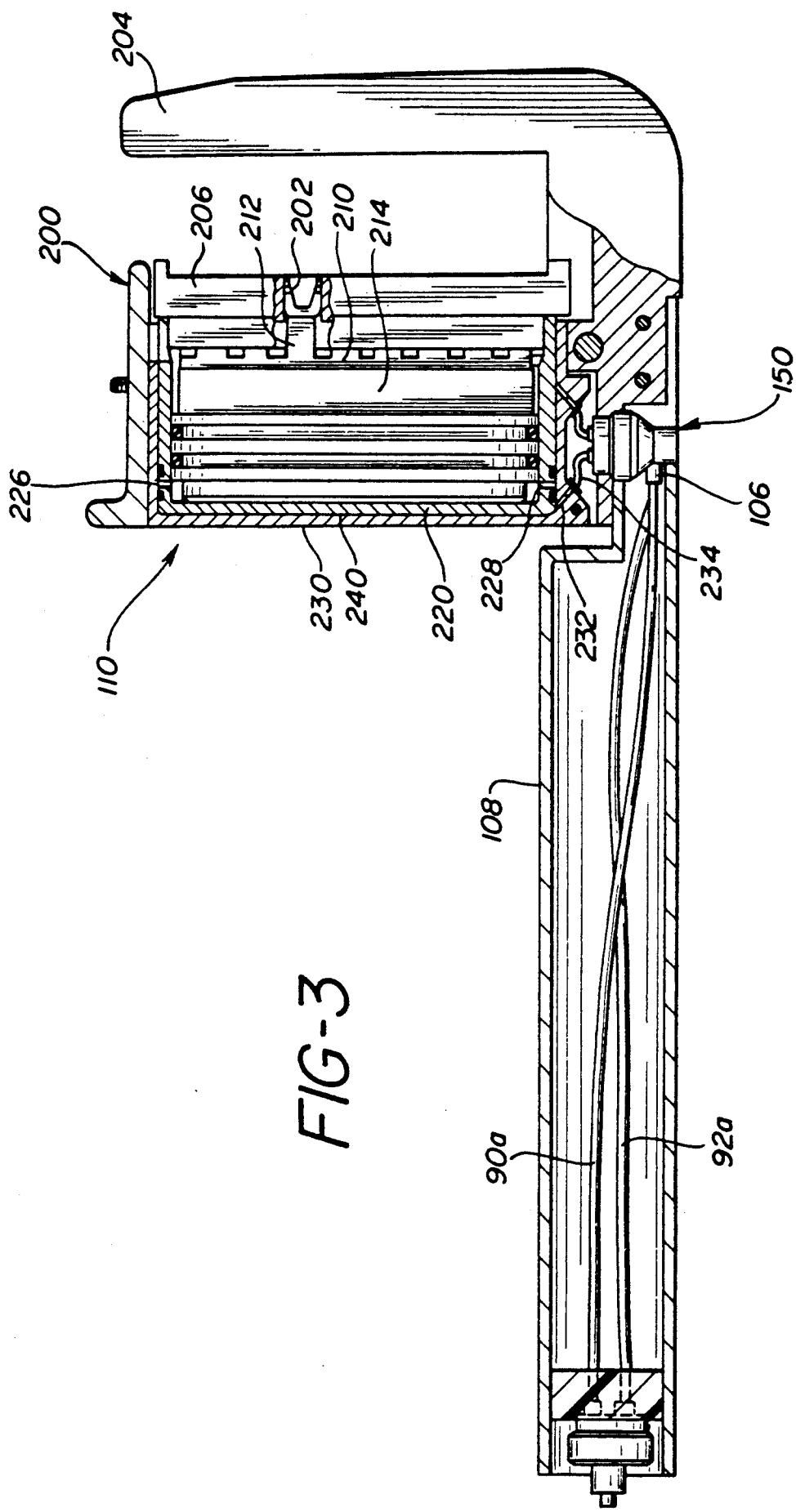
FIG. 3 is a partially cut away side plan view of a linear surgical stapler head.

As in FIGS. 2 and 3, the pressurized gas in passageway 90 and 92 of the handle portion 10 is conducted via passageways 90a, 92a to the clamping and stapling mechanisms in the stapler head 110 through pneumatic tubing and joints which connect the handle portion of the stapler to the stapler head through an interchangeable neck portion 108, as shown in FIGS. 1, 2 and 3. The neck portion 108 is connected to the handle portion and the stapler head 110 by conventional snap-lock fittings similar to those found on many pneumatic instruments, and by rotating unions, the latter being shown in FIG. 3. The rotating tube-passage unions allow the stapler head 110 and neck portion 108 to be rotated with respect to the handle portion 10 while maintaining the integrity of the pressurized gas lines.

FIGS. 2, 3, 4a and 4b are cross-sectional illustrations of a piston drive stapler head 110. The stapler head 110 includes jaw 200 which carries a plurality of staples 202 in a movable clamping and stapling mechanism. Opposite the jaw 200 is a stationary opposing jaw 204. The face of the stationary jaw which opposes the stapling mechanism comprises an anvil which clinches or bends the legs of metal staples which pass through the tissue between the jaws. When the staples are formed of absorbable polymeric materials, the stationary jaw will carry a cartridge of receivers which mate and retain the legs of the polymeric fasteners.

The staples 202 are located in pockets formed in a staple cartridge 206 on the jaw 200, with the legs of the staples directed towards stationary jaw 204. Behind the staple cartridge 206 is a staple pusher 210. The staple pusher 210 has fingers 212 directed toward the crowns of respective staples in the staple cartridge. Behind the staple pusher 210 is a driver piston 214. The driver piston is located inside a clamping piston 220, and is pneumatically sealed therein by two circumferential O-rings 216 and 218. The clamping piston 220 is located inside a piston housing 230. The clamping piston 220 is pneumatically sealed inside the piston housing by two circumferential O-rings 222 and 224. Between the O-rings are ports 226 and 228 which pass through the clamping piston. These ports are symmetrically located so that the clamping piston can be inserted into the piston housing with either end at the bottom.

Located at the rear of the piston housing is a passageway 232. This passageway 232 is connected to the right angle union 150 by a pneumatic tubing segment 234. Toward the front of the piston housing is a secondary passageway 236. This passageway is connected to union 150 by tubing segment 238. To the lower left of the staple head is the neck portion 108 of the stapler. The tubing in the neck portion is connected to the inlet ports of the right angle union 150 by pneumatic snap-fits 106.

When tissue to be stapled is located between the jaws 200 and 204 and it is desired to clamp the tissue between the jaws, the slide 70 is depressed and pressurized gas flows through the passageway 92 of the handle. The pressurized gas is carried through tubing in the neck portion 108 through the central passageway of the right angle union 150. The pressurized gas passes through tubing segment 234 and passageway 232 to the rear of the clamping piston 220. There, the gas is forced into the interface 240 between the clamping piston and the piston housing, where it expands and pushes the clamping piston forward toward the stationary jaw. As the clamping piston moves, it carries the driver piston, staple pusher, and staple cartridge with it. This will clamp the tissue between the staple cartridge and the stationary jaw. The clamping piston 220 is now in a position as indicated in phantom in FIG. 4a.

When the tissue is securely clamped between the jaws, the user unlocks a trigger safety and pulls the trigger 72 to implant staples. Pressurized gas flows through passageways 90, 90a, passageway 168 in union 150, and tubing segment 238 to passageway 236. Pressurized gas then flows through port 228 in the clamping piston and then to space 242 at the rear of the driver piston. When the expanding gas in this space pushes the driver piston 214 forward against the rear of the staple pusher 210, uniform pressure is applied to the pusher and its fingers. The fingers then drive the staples out of the pockets of the staple cartridge, through the tissue, and against the anvil or into the receivers of the stationary jaw. When the trigger is released, the pressurized gas to the driver piston and clamping piston is vented, releasing the jaw 200 from the stapled tissue.

FIG. 4 is similar to FIGS. 2, 3, 4a and 4b, but shows an alternate stapler head embodiment using balloon-like bladders. A driver bladder 250 is connected to tubing segment 238 and is located behind the driver piston 214 inside the clamping piston 220. A clamping bladder 252 is connected to tubing segment 234 and is located behind the clamping piston 220 inside the piston housing 230. As the clamping bladder 252 is inflated when the slide 70 is depressed, it expands and pushes the clamping piston 220 forward to clamp the tissue. When the trigger 72 is further depressed the driver bladder 250 is inflated, driving the driver piston 214 against the staple pusher and implanting staples in the tissue. The use of bladders obviates needs for O-ring seals around the pistons, which in this embodiment have no pneumatic properties. This embodiment allows the use of fully rectangular pistons, as the tolerancing of the bladder actuated pistons can be such as to prevent piston binding.

The embodiments of FIGS. 2, 3 and 4 are advantageous over pneumatic staplers which deliver pressurized gas to mechanical stapling mechanisms in the handle portion. In such staplers considerable energy is expended in actuating mechanical linkages extending from the handle and through the neck to the stapler head. In this invention, the pressurized gas is delivered directly at the stapler head. Thus, there is no ambiguity as to the force delivered during the clamping and stapling since the pressure regulated gas is delivered directly at the clamping and stapling members without energy loss.

Figure 5:
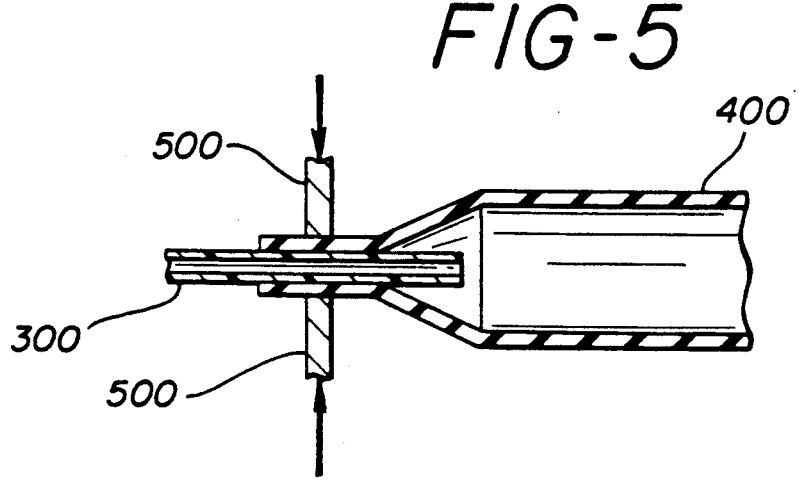
FIG. 5 is a view of the bladder and mandrel of the invention.

An alternate embodiment of the tubing and bladder configurations displayed in FIG. 4 is shown in FIG. 5. This bladder combination leading from either tubing segment is made so that the tube 300 extends into bladder 400 walls, as seen in FIG. 5. Thus, the chamber walls 500, created to fit the bladders within the stapler head 108, clamp the bladder 400 to the tube 300. Accordingly, there is reduced possibility of bladder material closing off the orifice of the pressurized supply tube. Additionally, there is no possibility of dimensional interference between the clamping mechanism and the tube 300 in that the wall size 500 is the same size as the outer diameter of bladder 400, which fits within the cavity formed for the bladder 400.

Figure 6:
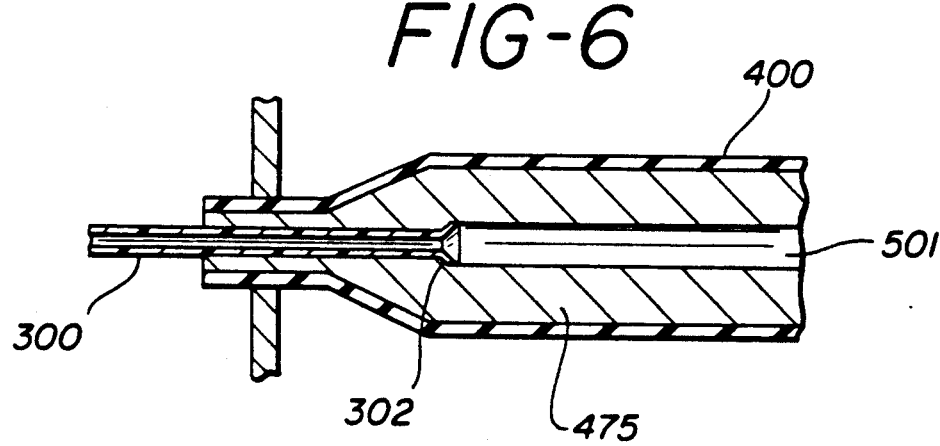
FIG. 6 is a similar view as in FIG. 5 showing an alternate connection.

Alternately, as in FIG. 6, the proximal end of a mandrel 475 is configured with an orifice 501 so as to accept the fluid supplied. A tube 300 can be attached by either chemical or mechanical means. Chemical means include such techniques as solvent bonding of the tube 300 to the mandrel 475 within the bladder 400. This is dependent upon appropriate selection of tube 300 and mandrel 475 materials as well as solvent. An appropriate supply tube might be polyurethane, and an appropriate mandrel material might be a polycarbonate. These could be attached through the use of solvents such as methylene chloride. Other polymer solvent choices should be apparent to those experienced in solvent bonding technology.

Connection is made as in FIG. 6. There, the supply tube 300 is flared at its end 302, and is introduced as in a reverse funnel receptacle in the mandrel 475, so that it is held in place. The tube 300 and mandrel 475 combination could then be processed by dipping it in a latex material so that latex material captures the tube 300 within the mandrel 475. Appropriate orientation of the tube 300 and mandrel 475 then restricts the connection and makes it impossible for the tube 300 to become dislodged. Of course, further consideration is that the supply tube 300 is part of the mandrel 475 itself.

Figure 7:
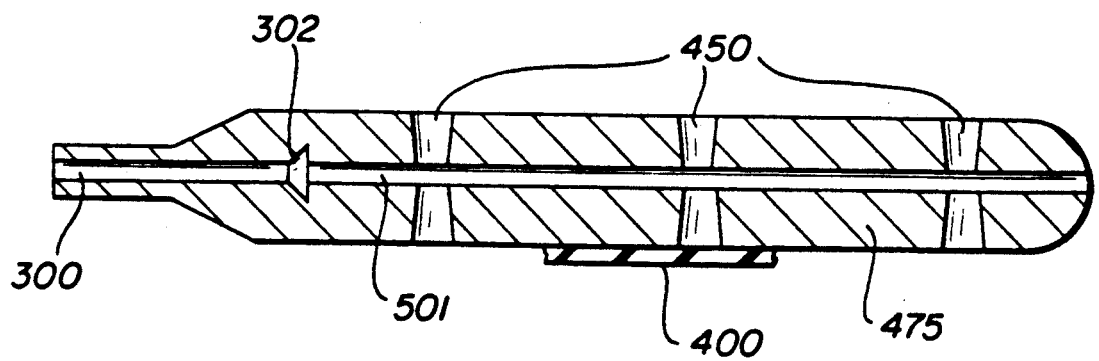
FIG. 7 is a cross-sectional view of the mandrel as seen in FIG. 6 showing locations of orifices within the mandrel.

As seen in FIG. 7, an orifice or orifices 450 could be introduced into the distal end of the mandrel 475 for the purpose of allowing flow of inflation fluid through the mandrel and into the bladder. Size and location of these holes is dependent upon material properties of the bladder 400 and the mandrel 475. Hole location must allow structural integrity of the mandrel while permitting maximum introduction of fluid in a minimum amount of time. Hole placement is crucial for elimination of any bladder seal-off problem. Mold release or talc could be selectively coated on the mandrel prior to bladder material addition. This allows bonding of the bladder material to the mandrel neck while permitting inflation separation in the functional area of the bladder 400.

In summary therefore, the tubing mandrel may be injection molded, or fabricated in some other means that would allow it to be permanently incorporated within the bladder. Supply line tubing is an integral part of the mandrel or could be permanently bonded to the bladder sub-assembly.

It is to be noted that the invention described herein is to be understood by the attached claims and their equivalents.

What is claimed is:

1. In a surgical stapler having an acuation mechanism connected to a stapling head containing a driving mechanism by means of a pneumatic stapling line, said driving mechanism including a staple driver and a stapling surface, and a driving piston to propel said driver, said piston attached to said pneumatic stapling line, said driving piston propelled by the inflation of a driving bladder seated behind said driving piston upon actuation of said actuation mechanism, the improvement comprising a driving bladder, and a tube embedded within said stapling head and containing a mandrel retaining the form of said driving bladder, said driving bladder filling upon introduction of pneumatic pressure into said tube.

2. In the surgical stapler of claim 1, said mandrel including an orifice extending the length of said bladder.

3. In the surgical stapler of claim 2, said mandrel including orifices extending from said main orifice.

4. In a surgical stapler having an actuation mechanism connected to a stapler head containing a driving mechanism by means of a pneumatic clamping line and a pneumatic stapling line, said driving mechanism including a staple driver and a stapling surface, a clamping piston attached to said pneumatic clamping line, said clamping piston capable of propelling said driving mechanism toward said stapling surface to clamp tissue between said driver and said stapling surface, and a driving piston to propel said driver, said driving piston attached to said pneumatic stapling line, said pneumatic clamping line propelling said clamping piston by means of a clamping bladder seated behind said clamping piston within a piston housing, said bladder filled by said pneumatic clamping line to drive said clamping piston when activated by said actuation mechanism, said driving piston propelled by the inflation of a driving bladder seated behind said driving piston upon actuation of said actuation mechanism, the improvement comprising a driving bladder and a clamping bladder, and a mandrel located within said driving bladder and a mandrel located within said clamping bladder, said respective mandrels connected to said respective bladders by means of tubes located within said stapler head.

5. In the stapler of claim 4, each of said mandrels having an orifice extending the entire length of said bladders.

6. In stapler of claim 5, said orifices including side orifices extending from said lengthwise orifice located within each of said mandrels.

* * * * *